(12) United States Patent
Pirzer et al.

(10) Patent No.: US 7,359,815 B2
(45) Date of Patent: Apr. 15, 2008

(54) METHOD AND DEVICE FOR CORRECTING A SPECTRUM

(75) Inventors: Martin Pirzer, Ettlingen (DE); Jürgen Sawatzki, Karlsruhe (DE)

(73) Assignee: Bruker Optik, GmbH, Ettlingen (DE)

( * ) Notice: Subject to any disclaimer, the term of this patent is extended or adjusted under 35 U.S.C. 154(b) by 68 days.

(21) Appl. No.: 11/358,697

(22) Filed: Feb. 21, 2006

(65) Prior Publication Data

US 2006/0212275 A1    Sep. 21, 2006

(30) Foreign Application Priority Data

Feb. 22, 2005    (DE) .................... 10 2005 009 195

(51) Int. Cl.
*G06F 15/00*    (2006.01)
(52) U.S. Cl. ....................................... 702/85
(58) Field of Classification Search ................ 702/85
See application file for complete search history.

(56) References Cited

U.S. PATENT DOCUMENTS

| | | | |
|---|---|---|---|
| 6,154,708 A * | 11/2000 | Koashi | ................. 702/40 |
| 2003/0195708 A1 | 10/2003 | Brown | |
| 2003/0231306 A1 | 12/2003 | Gornushkin et al. | |

OTHER PUBLICATIONS

Chad, et al., "Automated Method for Subtraction of Fluorescence from Biological Raman Spectra", Applied Spectroscopy, vol. 57, No. 11, pp. 1363-1367, 2003.

* cited by examiner

*Primary Examiner*—Tung S. Lau
(74) *Attorney, Agent, or Firm*—Law Offices of Paul E. Kudirka

(57) ABSTRACT

A method is provided for correcting at least one portion of a spectrum, in particular a Raman spectrum, by eliminating a baseline which is due to a perturbing spectrum, in particular due to a fluorescence spectrum, superimposed on the spectrum, wherein i) a convex envelope of the spectrum is determined, at least in the portion of the spectrum which is to be corrected, and ii) the convex part of the envelope lying below the spectrum is subtracted from the spectrum in the portion to be corrected. Before step i), iii) a convex function f is added to the spectrum in the portion to be corrected.

16 Claims, 5 Drawing Sheets

METHOD AND DEVICE FOR CORRECTING A SPECTRUM

RELATED APPLICATIONS

The present application claims priority of German patent application 10 2005 009 195.4 filed on Feb. 22, 2005.

BACKGROUND OF THE INVENTION

The invention relates to a method for correcting at least one portion of a spectrum, in particular a Raman spectrum, by eliminating a baseline which is due to a perturbing spectrum, in particular due to a fluorescence spectrum, superimposed on the spectrum.

The invention furthermore relates to a device for carrying out the method, as well as to a spectrometer device having a spectrometer, and to a computer-readable data medium on which a program which can carry out the method mentioned at the outset is stored.

Although the method according to the invention is described in the present description especially with reference to the example of correcting a Raman spectrum by eliminating a baseline which is due to a fluorescence spectrum superimposed on the spectrum, the method according to the invention can be used quite generally for correcting spectra on which an undesirable perturbing spectrum, which imposes an undesirable baseline on the desired spectrum, is superimposed.

Raman spectroscopy is an extensively used method for studying samples, for example biological substances.

An ideal Raman spectrum has Raman bands which lie on a straight baseline. A broadband perturbing spectrum or background spectrum, generally a fluorescence spectrum, is unfortunately often superimposed on Raman spectra. This perturbing spectrum may have very different curve profiles. In any event, a perturbing spectrum falsifies the desired Raman spectrum and makes it difficult to evaluate. Various methods have therefore already been employed in order to eliminate the perturbing spectrum from the Raman spectrum.

One method is to directly avoid a perturbing spectrum, such as a fluorescence spectrum, on the equipment side when recording the spectrum. However, these methods require modifications to the spectrometer and therefore increase the equipment outlay. Such equipment measures furthermore need to be readapted from sample to sample, which also leads to an increase in the time outlay for recording a spectrum besides increasing the equipment outlay.

Other methods, which do not entail the aforementioned disadvantages, consist in computationally eliminating the perturbing spectrum from the desired spectrum after recording the spectrum.

The US article by CHAD A. LIEBER and ANITA MAHADEVAN-JANSEN "Automated Method for Subtraction of Fluorescence from Biological Raman Spectra" published in APPLIED SPECTROSCOPY, 2003, pages 1362 to 1367, describes various methods for subtracting a fluorescence spectrum from a Raman spectrum. One of the methods described there consists in fitting a polynomial to the undesirable baseline of the recorded original or raw spectrum, which unfortunately makes it difficult to automate the correction method, requires a plurality of interventions by the user and is time-consuming, and furthermore needs to be readapted to the possible different curve profiles of perturbing spectra from case to case. A procedure described there as suitable for automation of the correction method is therefore a variant of the method of fitting the undesirable baseline by a polynomial, which operates with the aid of the least-squares method.

Automated use of the function, however, is virtually impossible since it is necessary for the degree of the polynomial to be established by the user before the calculation.

A better approach than this, on which the present invention is based, consists in finding a convex envelope of the spectrum and subtracting the convex part of the envelope lying below the spectrum from the spectrum in the portion to be corrected.

When a convex envelope of the spectrum is determined and the part of the convex envelope lying below the spectrum is subtracted from the spectrum, this method is also referred to as "rubber band" correction. Illustratively, this method can be interpreted as a rubber band, whose ends are fixed to the ends of the spectrum or the at least one portion of the spectrum which is to be corrected, being wrapped around the curve profile of the spectrum from below. The rubber band then fits itself against the curve profile of the spectrum. As seen from the x axis or from below, the rubber band assumes a convex polynomial configuration which corresponds to the undesirable baseline to be subtracted from the spectrum. If this is then taken away from the spectrum, the desired spectrum with a corrected baseline is obtained.

The "rubber band" correction method, however, does not lead to the desired elimination of the perturbing spectrum when it has a curve profile which comprises not only convex regions but also concave regions. Again illustratively using the example of the aforementioned rubber band, this means that the rubber band does not enter the concave regions of the perturbing spectrum, so that these concave regions are still present in the corrected Raman spectrum after subtracting the convex part of the envelope lying below the spectrum, which however continues to falsify the Raman spectrum.

There is therefore still a need for an improved method of correcting a spectrum.

SUMMARY OF THE INVENTION

It is therefore an object of the invention to provide a method of the type mentioned at the outset, which permits the desired elimination of the baseline due to the perturbing spectrum irrespective of the curve profile of the perturbing spectrum and allows at least semi-automation of the method, which does not require any elaborate interventions by the user, with moderate technical outlay.

It is also an object of the invention to provide a device of the type mentioned in the introduction, by which the method can be carried out in an at least semi-automated way requiring few interventions.

According to an aspect of the invention, a method for correcting at least one portion of a spectrum by eliminating a baseline which is due to a perturbing spectrum superimposed on said spectrum to be corrected is provided, comprising a sequence of steps i) adding a convex function f to said spectrum to be corrected at least in said portion to be corrected, ii) determining a convex envelope of said spectrum at least in said portion of said spectrum to be corrected, after said convex function f has been added to said spectrum in said portion to be corrected, and iii) subtracting that part of said convex envelope which lies below said spectrum from said spectrum in said portion to be corrected.

The method according to the invention therefore supplements the conventional "rubber band" correction with the step of adding a convex function f to the recorded spectrum. A convex function is a function whose tangents at any point of the function curve lie below the function curve. If only a portion of the spectrum is to be corrected, then the function f needs to be convex only in the portion to be corrected. The method according to the invention, however, not only can be carried out portion-by-portion but may also cover the entire range of interest of the spectrum at once.

The effect of adding a convex function f to the spectrum is that the baseline becomes less concave in regions of the spectrum when the baseline is concave, whereas regions of the spectrum whose baselines are convex or straight become convex or even more convex, but this is compensated for by the subsequent steps i) and ii) i.e. the steps of the conventional "rubber band" correction onto a straight baseline.

The method according to the invention is preferably carried out iteratively, i.e. the sequence of steps i), ii) and iii) is iterated repeatedly until the desired baseline is obtained, or in other words the perturbing baseline of the perturbing spectrum is eliminated.

The method according to the invention is suitable particularly for an at least semi-automated method, since the user now merely has to establish the number of iterations which may differ from case to case. Optionally, data preprocessing of the spectrum may also be carried out in order to remove any strong noise existing in the spectrum by smoothing the spectrum.

The method according to the invention has no restrictions in respect of the shape of the undesirable baseline due to the perturbing spectrum, and in particular it does not presuppose any modelling approaches such as the baseline being polynomial or the like. The present invention represents a substantial improvement of the conventional "rubber band" correction, which is effective even for perturbing spectra which impose a baseline having concave regions on the measured spectrum.

Preferred and advantageous configurations of the method according to the invention provide the following measures.

For instance, it is preferable for the function f to be determined in the portion to be corrected so that it is centred at least approximately with respect to the center of the portion to be corrected.

Furthermore, the function f is preferably determined in the portion to be corrected so that its function values at the ends of the portion to be corrected are about 5% to 15%, preferably about 10% greater in relation to the spectrum than in the center of the portion to be corrected.

In general, the function f is preferably of the form $f(x)=F|x-x_O|^n/N$ in the portion to be corrected, where $n>1$ and $x_O$ is the center of the portion of the spectrum to be corrected. F and N are constants.

In this case, F is determined as a fraction of the difference between the maximum $Y_{MAX}$ and the minimum $Y_{MIN}$ of the spectrum in the portion to be corrected.

Preferably, the factor F is determined as $(Y_{MAX}-Y_{MIN})/10$.

The normalization factor N is in this case preferably determined as $|x_E-x_O|^n$, where $x_E$ is the end of the portion to be corrected.

In a particularly preferred embodiment, the convex function f is a parabola of lowest order, i.e. $n=2$.

It was described above that the method is preferably carried out as an iteration method. The convex function f is in this case redetermined after each iteration according to the preferred configurations described above, and specifically with the aid of the correction state of the spectrum achieved in the preceding iteration stage. In this context the term "spectrum" refers to the (measured) original or raw spectrum before the method steps iii), i), ii) are carried out for the first time, at the first iteration to the spectrum obtained therefrom, in the second iteration to the spectrum obtained therefrom, etc.

As already mentioned, the method according to the invention can be applied not only to individual portions of the spectrum in succession, but equally to the entire range of interest of the spectrum, which although possibly leading to a lower accuracy of the correction nevertheless further reduces the time outlay of the correction.

According to another aspect of the invention, a device for correcting at least one portion of a spectrum by eliminating a baseline which is due to a perturbing spectrum superimposed on said spectrum to be corrected, comprising a computer unit which is configured so as to carry out a method is provided, comprising a sequence of steps i) adding a convex function f to said spectrum to be corrected at least in said portion to be corrected, ii) determining a convex envelope of said spectrum at least in said portion of said spectrum to be corrected, after said convex function f has been added to said spectrum in said portion to be corrected, and iii) subtracting that part of said convex envelope which lies below said spectrum from said spectrum in said portion to be corrected.

In a preferred configuration of the device, it comprises a controller via which the number of iterations of the method steps i), ii) and iii) and therefore the degree of correction or elimination of the undesirable baseline can be set.

The user of the device advantageously then only needs to operate the controller, in order to eliminate the perturbing spectrum and the undesirable baseline due to it from the spectrum in a thereby semi-automated way.

In this context, the device preferably comprises a display for displaying the spectrum and for tracking the degree of correction of the baseline set via the controller.

The user of the device can therefore track the effect of the degree of correction set via the controller on the display, or a PC monitor, and accordingly adjust the controller via visual inspection so that the desired baseline correction is achieved. In this case, the user can also establish when an overcorrection takes place and which degree of correction is optimal.

According to still another aspect of the invention, a spectrometer device is provided comprising a spectrometer and a device for correcting at least one portion of a spectrum by eliminating a baseline which is due to a perturbing spectrum superimposed on said spectrum to be corrected, comprising a computer unit which is configured so as to carry out a method comprising a sequence of steps i) adding a convex function f to said spectrum to be corrected at least in said portion to be corrected, ii) determining a convex envelope of said spectrum at least in said portion of said spectrum to be corrected, after said convex function f has been added to said spectrum in said portion to be corrected, and iii) subtracting that part of said convex envelope which lies below said spectrum from said spectrum in said portion to be corrected.

According to still another aspect of the invention, a computer-readable data medium is provided on which a program which can carry out a method for correcting at least one portion of a spectrum by eliminating a baseline which is due to a perturbing spectrum superimposed on said spectrum to be corrected is stored, said method comprising a sequence of steps
i) adding a convex function f to said spectrum to be corrected at least in said portion to be corrected,
ii) determining a convex envelope of said spectrum at least in said portion of said spectrum to be corrected, after said convex function f has been added to said spectrum in said portion to be corrected, and
iii) subtracting that part of said convex envelope which lies below said spectrum from said spectrum in said portion to be corrected.

Other advantages and features will be found in the following description and the appended drawings.

It is to be understood that the features mentioned above and yet to be explained below may be used not only in the combination respectively indicated, but also in other combinations or separately, without departing from the scope of the present invention.

BRIEF DESCRIPTION OF THE DRAWINGS

The above and further advantages of the invention may be better understood by referring to the following description in conjunction with the accompanying drawings in which.

DETAILED DESCRIPTION

Figure 1:
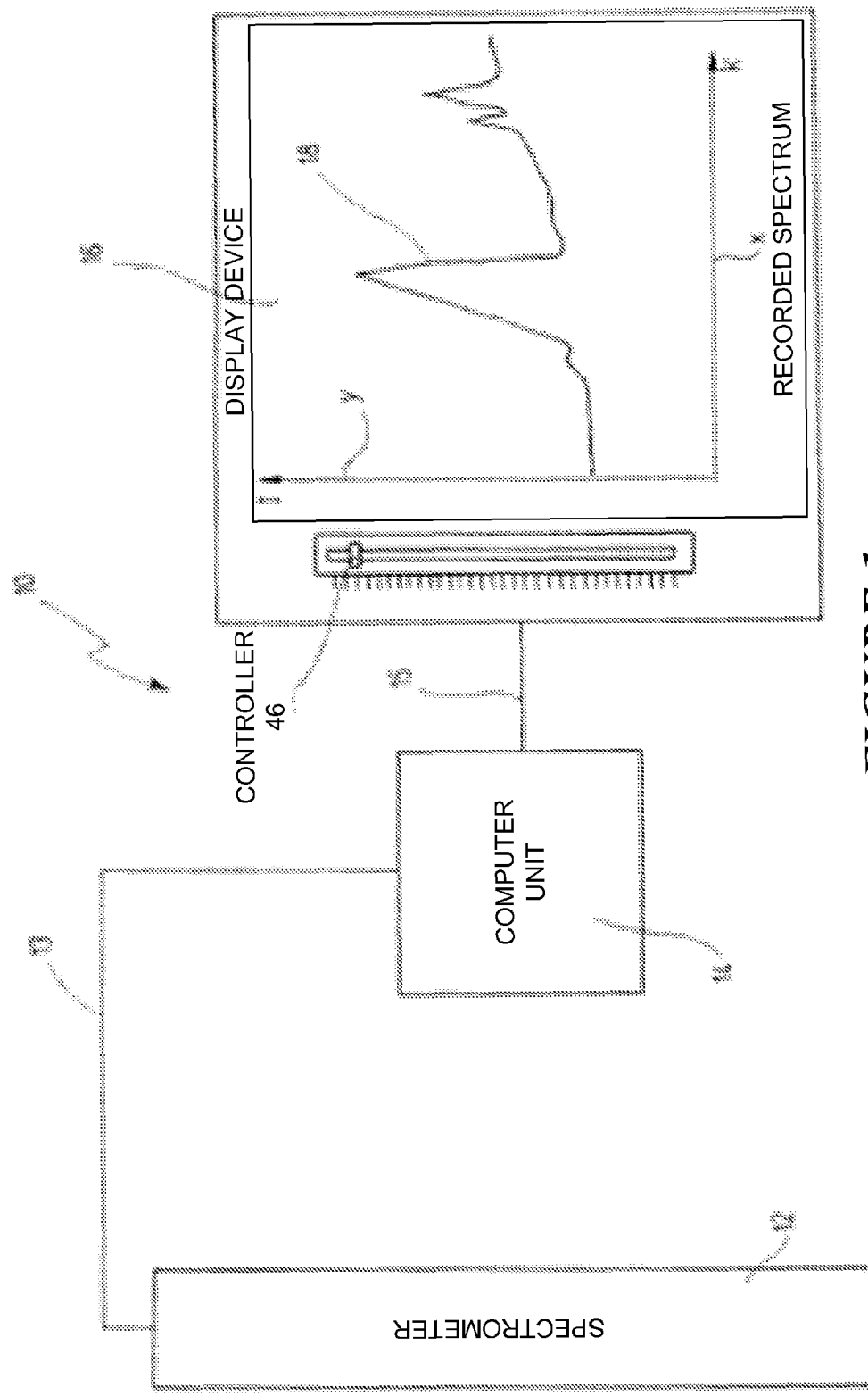
FIG. 1 very schematically shows an overall representation of a spectrometer device.

FIG. 1 very schematically represents a spectrometer device which is provided with the overall reference numeral 10.

The spectrometer device 10 comprises a spectrometer 12, in particular a Raman spectrometer, with which a Raman spectrum of a sample (not shown) can be recorded. Alternatively, the spectrometer 12 may be an IR spectrometer or a combined IR/Raman spectrometer. The spectrum measured by the spectrometer 12 is transmitted via a signal line 13 to a computer unit 14, which is connected via a further line 15 to a display device 16 on which a recorded spectrum 18 can be visually represented. For example, the spectrum 18 is represented as a graph of the intensity I of the absorption as a function of the wavenumber k. The intensity I therefore represents the y axis and the wavenumber k represents the x axis of the spectrum 18.

Figure 2:
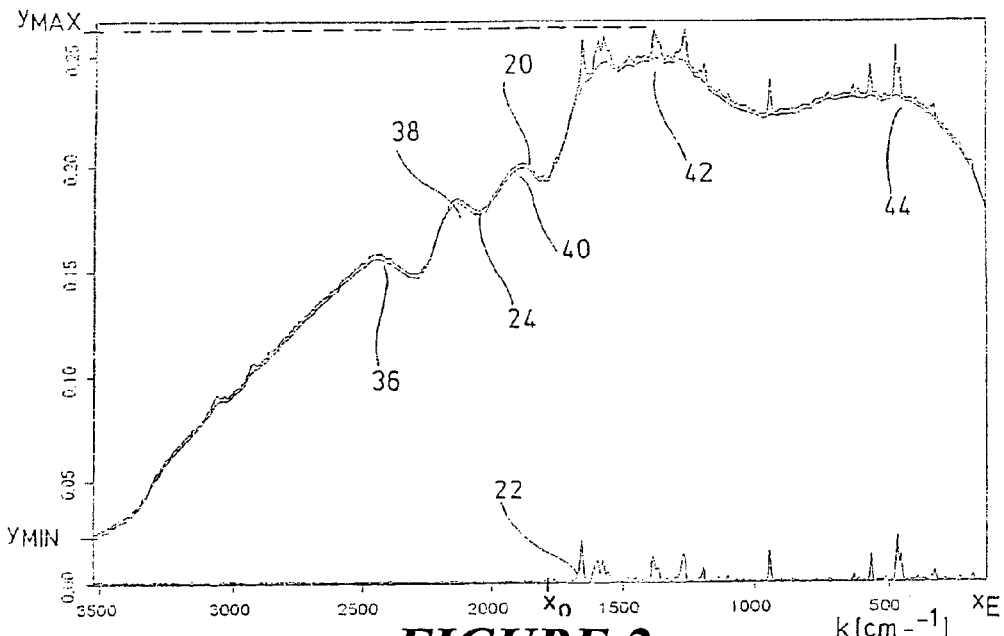
FIG. 2 shows a recorded Raman spectrum before correction (top curve) and after correction (bottom curve) by eliminating a baseline (center curve) which is due to a perturbing spectrum superimposed on the Raman spectrum.
Figure 3:
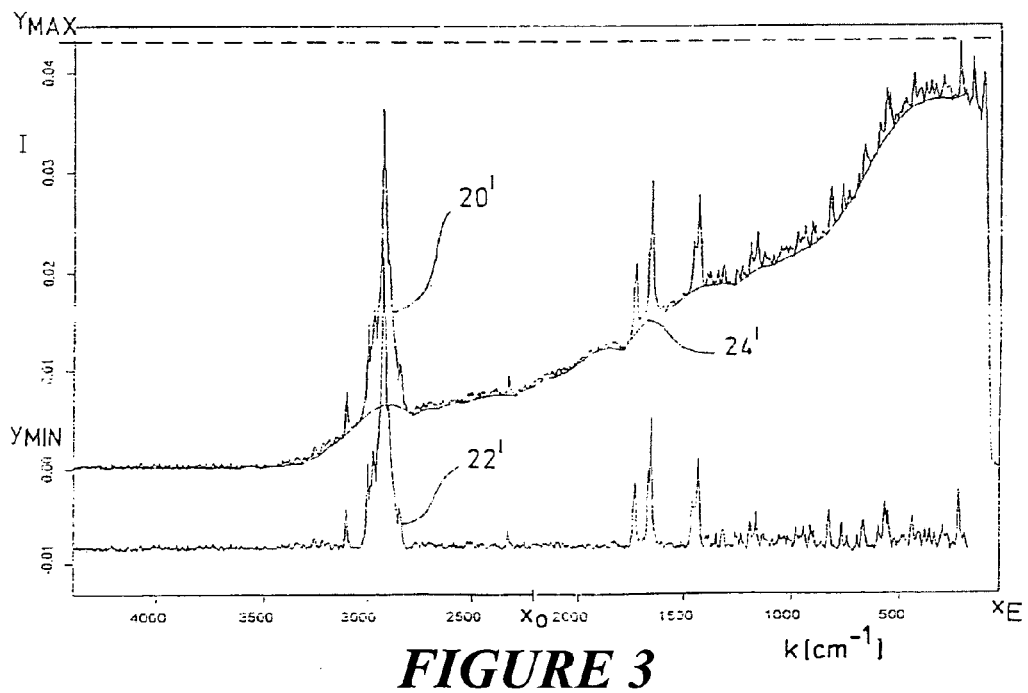
FIG. 3 shows a further Raman spectrum before and after correction, similarly as FIG. 2.

Two different Raman spectra measured by the spectrometer 12 are represented in FIGS. 2 and 3 by 20 and 20' (top curves in FIGS. 2 and 3).

Typically, however, Raman spectra do not have a curve profile corresponding to the curves 20 and 20' but possess a straight baseline, as represented by the curves 22 and 22' in FIGS. 2 and 3. The curves 22 and 22' therefore represent the "ideal" Raman spectra.

A perturbing spectrum, typically a fluorescence spectrum, which is represented by the curves 24 and 24' in FIGS. 2 and 3, is therefore superimposed on the Raman spectra according to the curves 20 and 20' measured by the spectrometer 12.

The perturbing spectrum imposes a baseline corresponding to the curves 24 and 24' on the Raman spectra actually to be measured, which perturbs the evaluation of the Raman spectra according to the curves 20 and 20'. The undesirable baselines 24 and 24' therefore need to be eliminated from the spectra according to the curves 20 and 20' by means of a suitable method. An exemplary embodiment of a relevant method will be described in more detail below with reference also to FIG. 4.

The method described below is applied to the entire range of interest of the spectrum curves 20 and 20', which are represented in FIGS. 2 and 3, although it should be understood here that the method may also be applied portion-by-portion, i.e. successively to subportions of the curve profiles represented in FIGS. 2 and 3.

Figure 4:
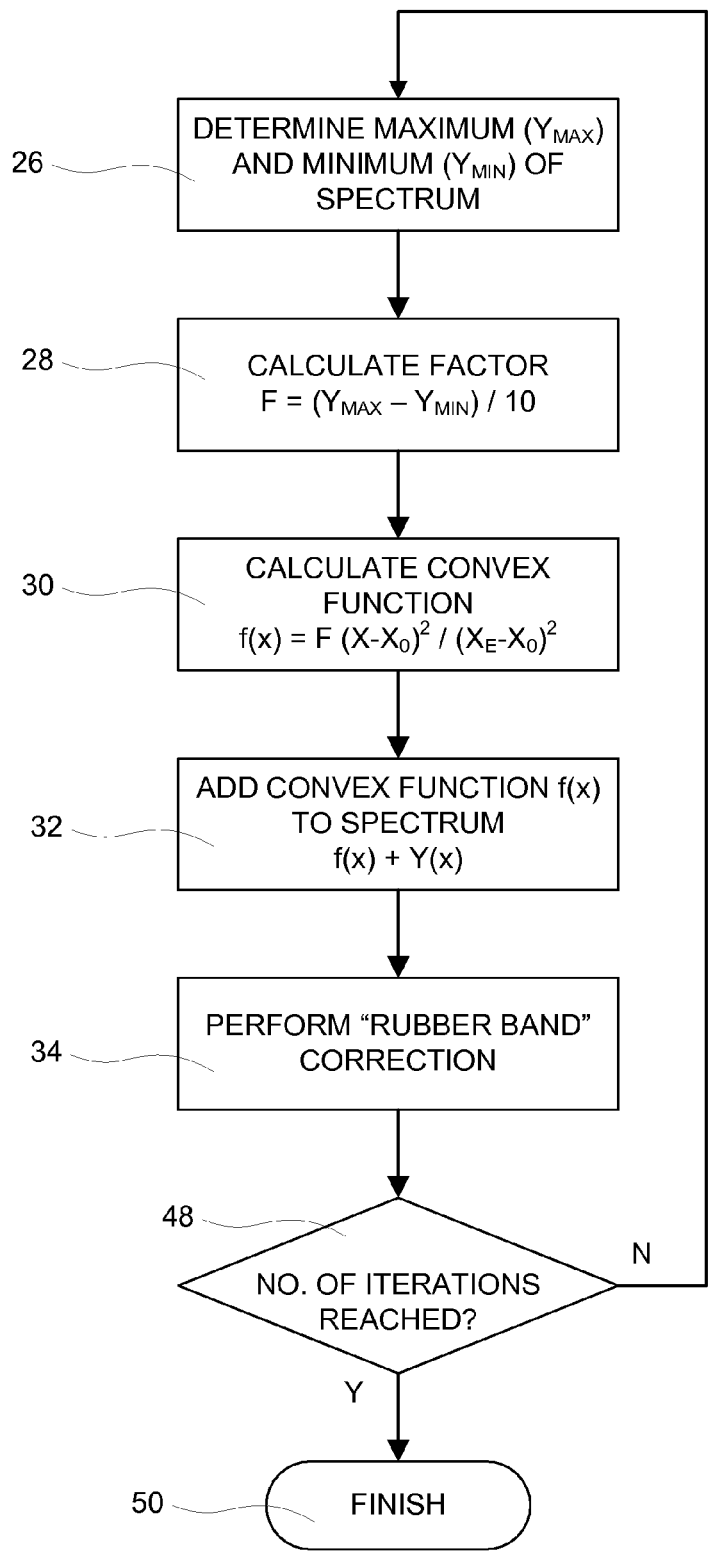
FIG. 4 shows a flow chart of a method for correcting a spectrum by eliminating a baseline which is due to a perturbing spectrum superimposed on the spectrum.

According to FIG. 4, the y maximum $Y_{MAX}$ and the y minimum $Y_{MIN}$ of the recorded raw spectrum (curve 20 or curve 20') are found in a first step 26. $Y_{MAX}$ and $Y_{MIN}$ are respectively represented on the y axis in FIGS. 2 and 3.

In the next step 28, a factor F is calculated from $Y_{MAX}$ and $Y_{MIN}$ according to the equation $F=(Y_{MAX}-Y_{MIN})/10$.

In the next step 30, a convex function f is calculated in the form of a parabola, and specifically $f(x)=F \cdot (x-x_O)^2/(x_E-x_O)^2$, where $x_O$ (cf. FIGS. 2 and 3) is the center of the portion of interest of the spectrum and $x_E$ is the end of the portion of interest of the spectrum which, as already mentioned, covers the entire range of the measured spectrum in the present exemplary embodiment according to FIGS. 2 and 3.

The parabola f(x) is 10% higher at the ends $x_E$ in relation to the spectrum according to the curves 20 and 20' than in the center $x_o$.

The function f(x) may generally be of the form:

$f(x)=F|x-x_O|^n/N$, where n>1 and F and N are constants, F preferably being selected so that f at the ends of the range of interest of the spectrum is about 10% greater in relation to the spectrum than in the center of the range, and where N is preferably determined as $|x-x_E|^n$.

In the next step 32, the convex function f(x) is now added to the spectrum Y(x) according to the curves 20 and 20'.

In the subsequent step 34, the conventional "rubber band" correction is applied to the sum of the convex function f(x) and the spectrum Y(x). This consists in finding a convex envelope for the sum of the convex function f(x) and the spectrum Y(x) as obtained in step 32, only the convex part of the envelope lying below the curve f(x)+Y(x) being taken. The convex part of the envelope lying below the "new" curve of the spectrum found according to step 32 is then subtracted from this curve.

The steps 26 to 34 are iterated repeatedly in this sequence, $Y_{MAX}$ and $Y_{MIN}$ now being calculated in step 26 no longer with the aid of the original spectrum but with the aid of the spectrum as obtained after the preceding step 34, etc.

The method according to steps 26 to 34 with a suitable number of iterations is particularly suitable when the baseline due to the perturbing spectrum, like the baseline 24, has pronounced concave regions 36, 38, 40, 42 and 44, as represented in FIG. 2. The effect of adding a convex function to the "new" spectrum obtained after each iteration is that the concave regions 36, 38, 40, 42 and 44 become less and less concave so that these concave regions are smoothed after an appropriate number of iterations, as represented by the curve 22 in FIG. 2.

The method has no effect on portions which are already straight or convex, since the "rubber band" correction is also carried out at each iteration.

The method described above is stored in the computer unit 14 and, for example, implemented in the operating software of the spectrometer device 10.

The only intervention which the user of the spectrometer device 10 must carry out is to set the number of iterations of the method steps 26 to 34 by means of a controller 46 (FIG. 1). The controller 46 may, for example, be a controller represented on the display device 16 and operable via the PC keyboard or a mouse, as represented in FIG. 1, in which case the degree of correction of the spectrum 18 (or 20 or 20') respectively set when adjusting the controller 46 can be visually tracked.

It is nevertheless possible to provide a fully automated mode in which there is no controller 46, but instead the number of iterations of the method steps 26 to 34 may already be definitively entered, which, for example, leads to good results when spectra of the same type are to be corrected.

In the method sequence according to FIG. 4, a step 48 is implemented which contains a query as to whether or not the number of iterations has been reached. The method is terminated at 50 if the number of iterations which has been preset or adjusted via the controller 46 is reached, otherwise a further iteration of the method is carried out.

Figure 5:
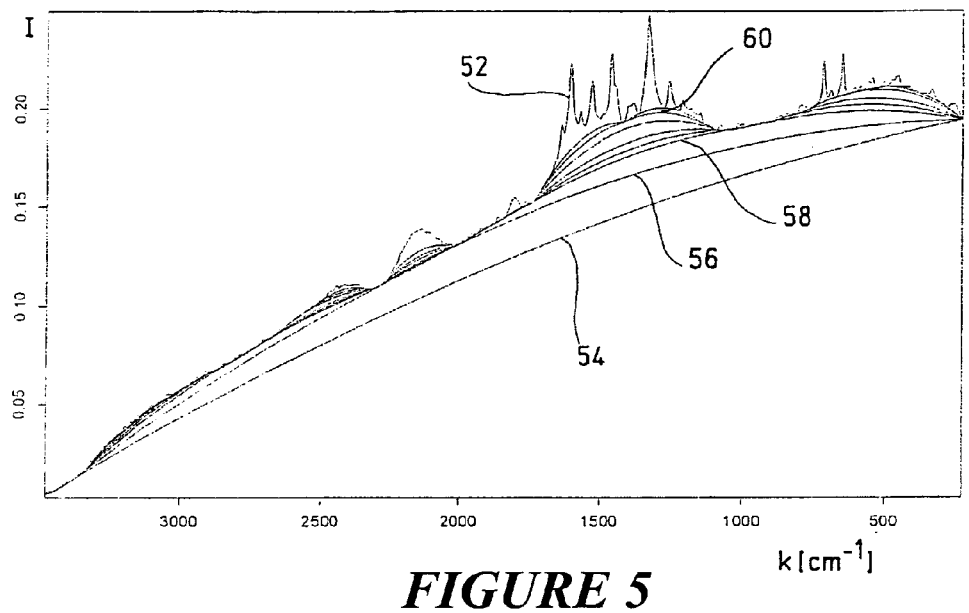
FIG. 5 shows a further Raman spectrum before correction (top curve) with a multiplicity of curves, which illustrate the way in which the perturbing baseline is found as a function of the number of iterations of the method according to FIG. 4, being indicated below the recorded raw spectrum.
Figure 6:
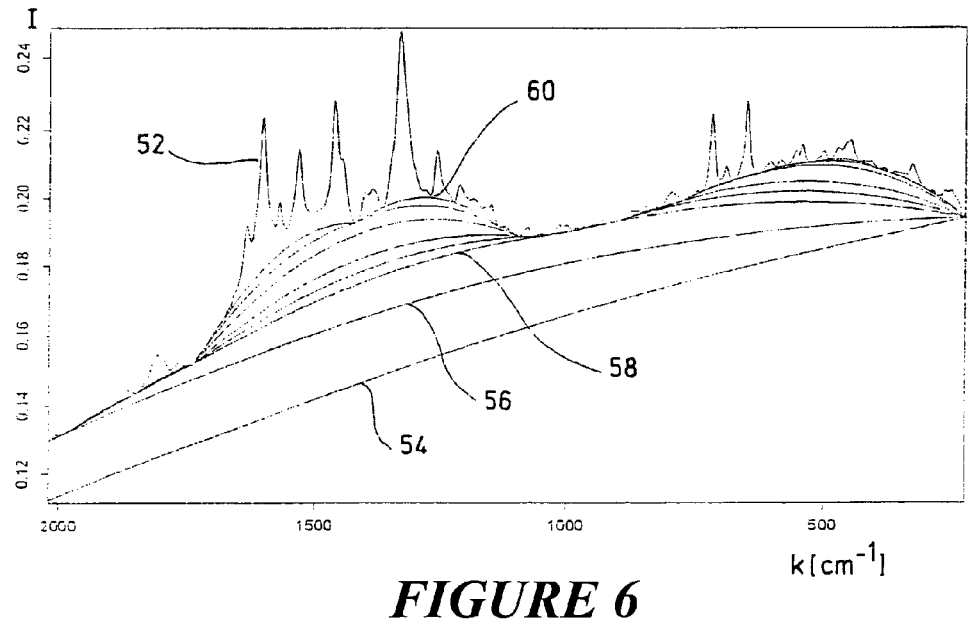
FIG. 6 shows a detail of FIG. 5 on an enlarged scale.

FIGS. 5 to 7 again illustrate the effectiveness of the method with the aid of a further spectrum. A curve 52 represents a Raman spectrum measured by the spectrometer 12, before its correction.

A multiplicity of curves 54, 56, 58 etc., which correspond to the curve profiles of the perturbing baseline of the perturbing spectrum as found after a particular number of iterations of the method, are represented below the curve 52.

The curve 54 represents the perturbing baseline found before the first iteration, the curve 56 after the first iteration, the curve 58 after the third iteration etc., with a curve 60 representing the perturbing baseline found after 22 iterations. It can be seen that the curves 54, 56, 58, i.e. with an increasing number of iterations, merge more and more into the concave regions of the spectrum and become closer and closer to the true profile of the perturbing baseline.

Figure 7:
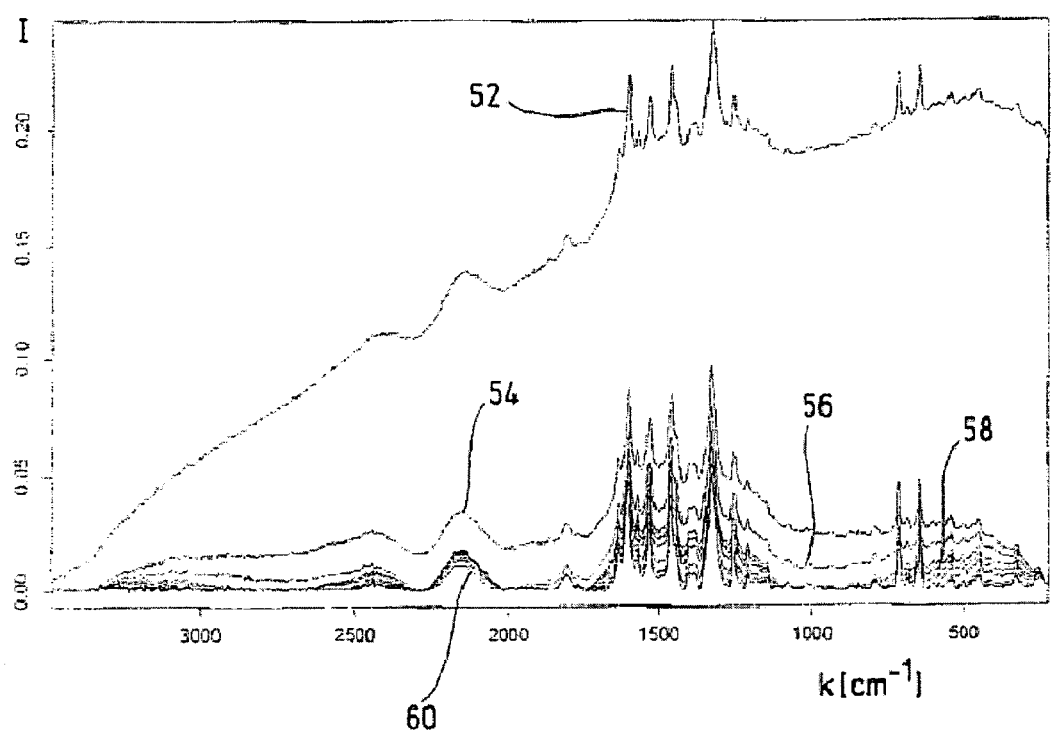
FIG. 7 shows a representation comparable to FIG. 5 where the intermediate correction states of the spectrum, obtained respectively after a particular number of iterations of the correction method, are represented in a multiplicity of curves.

FIG. 7 represents the correction states of the spectrum 52 respectively achieved after a corresponding number of iterations, the partly corrected curve profiles of the spectrum 52 belonging to the baselines respectively found after the corresponding iterations being represented in FIG. 7. The curve 60 represents the desired corrected spectrum.

What is claimed is:

1. A method for correcting at least one portion of a spectrum by eliminating a baseline which is due to a perturbing spectrum superimposed on said spectrum to be corrected, comprising a sequence of steps:

i) collecting from a spectrometer, spectral data representing the spectrum to be corrected, ii) storing the spectral data in a memory, iii) adding data generated from a convex function f to said stored spectral data at least in said portion to be corrected, wherein the convex function f is a function whose tangents at any point of its function curve lie below its function curve at least in said portion to be corrected, iv) determining data representing a convex envelope of said stored spectral data at least in said portion of said spectrum to be corrected, after said convex function f data has been added to said stored spectral data in said portion to be corrected, and v) subtracting that part of said convex envelope data which lies below said spectrum from said stored spectral data in said portion to be corrected so that the stored spectral data represents a corrected spectrum.

2. The method of claim 1, wherein said function f is determined in said portion to be corrected such that said function f is centered at least approximately with respect to the center of said portion to be corrected.

3. The method of claim 1, wherein said function f is determined in said portion to be corrected such that function values of said function f at ends of said portion to be corrected are greater than the function value of the function f in a center of said portion to be corrected by about 5% to 15% of a difference between a maximum value of the stored spectrum data and the minimum value of the stored spectrum data.

4. The method of claim 1, wherein said function f is determined in said portion to be corrected such that function values of said function f at ends of said portion to be corrected are greater than the function value of the function f in a center of said portion to be corrected by about 10% of a difference between a maximum value of the stored spectrum data and the minimum value of the stored spectrum data.

5. The method of claim 1, wherein said function f is of the form $f(x)=F \cdot |x-x_O|^n/N$ in said portion to be corrected, where n>1 and $x_O$ is a center of said portion of said spectrum which is to be corrected.

6. The method of claim 1, wherein said at least one portion is the entire range of interest of said spectrum to be corrected.

7. The method of claim 1, wherein said sequence of steps i), ii) and iii) is iterated repeatedly until a desired baseline is obtained.

8. The method of claim 5, wherein F is determined as a fraction of the difference between a maximum ($Y_{MAX}$) and a minimum ($Y_{MIN}$) of said spectrum in said portion to be corrected.

9. The method of claim 5, wherein N is determined as $|x_E-x_O|^n$, where $x_E$ is an end of said portion to be corrected.

10. The method of claim 5, wherein n =2.

11. The method of claim 8, wherein F is determined as $(Y_{MAX}-Y_{MIN})/10$.

12. A device for correcting at least one portion of a spectrum by eliminating a baseline which is due to a perturbing spectrum superimposed on said spectrum to be corrected, comprising a computer unit which is configured so as to carry out a method comprising a sequence of steps:

i) adding a convex function f to said spectrum to be corrected at least in said portion to be corrected, wherein the convex function f is a function whose tangents at any point of its function curve lie below its function curve at least in said portion to be corrected, ii) determining a convex envelope of said spectrum at least in said portion of said spectrum to be corrected, after said convex function f has been added to said spectrum in said portion to be corrected, and iii) subtracting that part of said convex envelope which lies below said spectrum from said spectrum in said portion to be corrected.

13. The device of claim 12, further comprising a controller for adjusting a number of iterations of said sequence of steps i), ii), iii) and therefore a degree of correction of said baseline via said controller.

14. The device of claim 13, further comprising a display device for displaying said spectrum and for tracking said degree of correction of said baseline set via said controller.

15. A spectrometer device, comprising a spectrometer and a device for correcting at least one portion of a spectrum by eliminating a baseline which is due to a perturbing spectrum superimposed on said spectrum to be corrected, said device for correcting comprising a computer unit which is configured so as to carry out a method comprising a sequence of steps:

i) adding a convex function f to said spectrum to be corrected at least in said portion to be corrected, wherein the convex function f is a function whose tangents at any point of its function curve lie below its function curve at least in said portion to be corrected, ii) determining a convex envelope of said spectrum at least in said portion of said spectrum to be corrected, after said convex function f has been added to said spectrum in said portion to be corrected, and iii) subtracting that part of said convex envelope which lies below said spectrum from said spectrum in said portion to be corrected.

16. A computer-readable storage medium on which a program which can carry out a method for correcting at least one portion of a spectrum by eliminating a baseline which is due to a perturbing spectrum superimposed on said spectrum to be corrected is stored, said method comprising a sequence of steps:

i) adding a convex function f to said spectrum to be corrected at least in said portion to be corrected, wherein the convex function f is a function whose tangents at any point of its function curve lie below its function curve at least in said portion to be corrected, ii) determining a convex envelope of said spectrum at least in said portion of said spectrum to be corrected, after said convex function f has been added to said spectrum in said portion to be corrected, and iii) subtracting that part of said convex envelope which lies below said spectrum from said spectrum in said portion to be corrected.

* * * * *